United States Patent [19]

Schneider et al.

[11] 4,239,688
[45] Dec. 16, 1980

[54] HERBICIDAL N-(HALOACETYL)-N-(N'-METHYLENEPYR-ROLIDONYL-2-MERCAPTOALKYLANI-LINES

[75] Inventors: Louis Schneider, Elizabeth; David E. Graham, Westfield, both of N.J.

[73] Assignee: GAF Corporation, New York, N.Y.

[21] Appl. No.: 935,354

[22] Filed: Aug. 21, 1978

[51] Int. Cl.³ .................. A01N 9/22; C07D 207/27
[52] U.S. Cl. .................. 260/326.43; 71/95; 260/326.55
[58] Field of Search .................. 260/326.43

[56] References Cited

U.S. PATENT DOCUMENTS

| | | | |
|---|---|---|---|
| 3,207,813 | 9/1965 | Harvey | 260/834 |
| 3,769,301 | 10/1973 | Olin | 260/326.45 |
| 4,014,679 | 3/1977 | Pemonnet | 71/118 |

FOREIGN PATENT DOCUMENTS

| | | |
|---|---|---|
| 909706 | 3/1968 | Canada . |
| 818573 | 7/1969 | Canada . |
| 1078071 | 8/1967 | United Kingdom . |
| 1078072 | 8/1967 | United Kingdom . |

OTHER PUBLICATIONS

Kirk–Othmer, "Encyclopedia of Chemical Technology", vol. 12, pp. 111–112 (1954).

Chupp, "J. Org. Chem.", 34, p. 1192 (1969).

Primary Examiner—Donald G. Daus
Assistant Examiner—Lisa Jones
Attorney, Agent, or Firm—Walter C. Kehm; Walter Katz

[57] ABSTRACT

Herbicidal compounds having the formula:

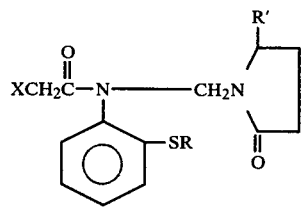

where
R is alkyl having 1–6 carbon atoms, alkenyl having 2–6 carbon atoms, cycloalkyl having 4–6 carbon atoms, unsubstituted or substituted with alkyl of 1–4 carbon atoms, or alkyleneoxyalkyl of 2–8 carbon atoms,
R' is hydrogen or alkyl of 1–3 carbon atoms, and,
X is chloro or bromo.
are provided herein.

The compounds of the invention are effective herbicides, particularly against wild grasses.

16 Claims, No Drawings

HERBICIDAL N-(HALOACETYL)-N-(N'-METHYLENEPYR-ROLIDONYL-2-MERCAPTOALKYLANILINES

BACKGROUND OF THE INVENTION

1. Field of the Invention

This invention relates to novel N-(haloacetyl)-N-(N'-methylenepyrrolidonyl)-2-mercaptoalkylanilines which are useful herbicides.

2. Description of the Prior Art

U.S. Pat. Nos. 3,769,301 and 3,907,544 disclose related N-(acyl-tert-amidoalkyl)acetanilides, including N-methylenepyrrolidonyl derivatives; however, these compounds are substituted with 2,6-dialkyl groups only.

SUMMARY OF THE INVENTION

This invention describes herbicidal N-(haloacetyl)-N-(N'-methylenepyrrolidonyl)-2-mercaptoalkylanilines having the formula:

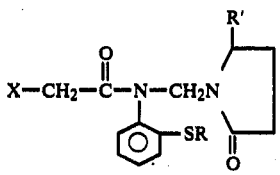

where
R is alkyl having 1–6 carbon atoms, alkenyl having 2–6 carbon atoms, cycloalkyl having 4–6 carbon atoms, unsubstituted or substituted with alkyl of 1–4 carbon atoms, or alkyleneoxyalkyl of 2–8 carbon atoms,
R' is hydrogen or alkyl of 1–3 carbon atoms, and,
X is chloro or bromo.

DETAILED DESCRIPTION OF THE PREFERRED EMBODIMENTS

The herbicidally active compounds of the present invention may be obtained by a four-step process. In the first step, 2-nitrothiophenol is reacted with an alkyl halide in the presence of an acid acceptor to yield 2-alkoxythioalkoxynitrobenzene. In the second step, the nitro group is reduced to the corresponding aniline. The third step of the process comprises reacting the aniline with a suitable N-methylolpyrrolidone to form the corresponding N-(N'-methylenepyrrolidonyl) intermediate. Finally, in step four, the intermediate is suitably acylated with a haloacetyl halide to form the desired compounds.

The reaction sequence is as follows:

Step 1

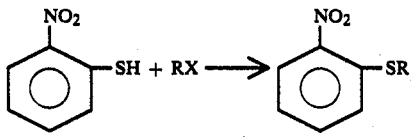

where
R is alkyl having 1–6 carbon atoms, alkenyl having 2–6 carbon atoms, cycloalkyl having 4–6 carbon atoms, unsubstituted or substituted with alkyl of 1–4 carbon atoms, and alkyleneoxyalkyl of 2–8 carbon atoms, and X is a halogen.

Step 2

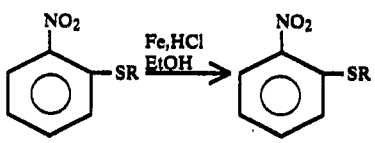

Step 3

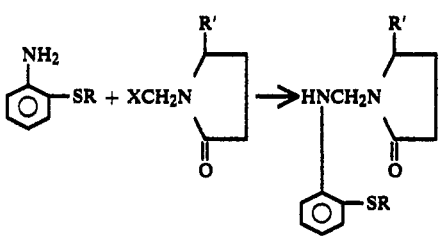

where
R' is hydrogen or alkyl of 1–3 carbon atoms, and
X is a halogen.

Step 4

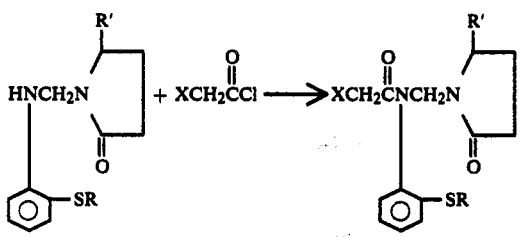

where X is chloro or bromo.

As used herein, the term "alkyl" includes both straight and branched chained hydrocarbons.

The compounds of this invention are especially useful as agricultural herbicides. They show particularly effective herbicidal activity against Japanese millet, foxtail millet and crabgrass.

Usually they are applied to the soil at the rate of about 1 to 25 lbs. per acre, or as a foliar spray on the weeds at concentrations of about 30 to 260 ppm., depending on various circumstances of the susceptibility of the weed to the herbicide, the weather, the stage of growth and various other factors. The material also may be applied as a dust. As a dust, it is practical to extend it with diluents, such as bentonite, chalk, clay, diatomaceous earth, fullers earth, mica, ground slate or any of the other usual carriers for agricultural chemicals.

As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

Following are examples of preparation of the compounds of the invention and are present by way of illustration and are not intended to be limiting unless otherwise specified.

EXAMPLE 1

N-Chloroacetyl-N-(N'-Methylenepyrrolidonyl)-2-Methylmercaptoaniline

A. N-(N'-Methylenepyrrolidonyl)-2-Methylmercaptoaniline

2-Methylmercaptoaniline (50.0 g, 0.36 mole), N-methylol-2-pyrrolidone (41.3 g, 0.36 mole) and toluene (145 cc) were refluxed under azeotropic conditions until the stoichiometric amount of water was removed. The reaction was washed succesively with 100 cc of 10% hydrochloric acid, 100 cc of 10% sodium carbonate and finally with water. The toluene phase was dried over magnesium sulfate and removed by rotary evaporation. The product (69 g, 81.5% yield) was isolated as an oil.

B. N-Methylenepyrrolidonyl-2-methylmercaptoaniline (11.8 g., 0.05 mole), toluene (100 cc) and sodium carbonate (5.8 g, 0.055 mole) were cooled to 5° C., and a solution of chloroacetyl chloride (6.2 g, 0.055 mole) is toluene (20 cc) was added in one hour. The temperature of the mixture then was slowly raised to 75°–80° C. and maintained at that temperature for one hour. The reaction mixture then was washed with 100 cc water, and the toluene removed by rotary evaporation. The product (8.5 g) was obtained in 54.5% yield by crystallization from hexane; 102.5°–104° C.

EXAMPLE 2

N-Chloroacetyl-N-(N'-Methylenepyrrolidonyl)-2-Ethylmercaptoaniline

2-Ethylmercaptoaniline, N-methylolpyrrolidone and toluene were condensed with the removal of water in a similar manner as described in Example 1. The intermediate formed then was condensed with chloroacetyl chloride in toluene in the presence of sodium carbonate, to form the desired product.

EXAMPLE 3

N-Chloroacetyl-N-(5-Methyl-N'-Methylenepyrrolidonyl)-2-Methylmercaptoaniline

2-Methylmercaptoaniline, N-methylol-5-methylpyrrolidone and toluene were reacted in a similar manner as described in Example 1. The intermediate formed was condensed with chloroacetyl chloride in toluene in the presence of sodium carbonate to form the desired product.

EXAMPLE 4

N-Chloroacetyl-N-(N'-Methylenepyrrolidonyl)-2-Isopropylmercaptoaniline

A. 2-Isopropylmercaptoaniline

2-Nitrothiophenol, 2-bromopropane, potassium carbonate and acetone were refluxed for several hours. The solvent then was removed by rotary evaporation. The crude product was partitioned between methylene chloride and a 10% sodium carbonate solution. The organic phase was distilled to yield 2-isopropylmercaptonitrobenzene.

B. This intermediate was reduced to the corresponding aniline by reduction with iron, concentrated hydrochloric acid and ethanol. The mercaptoaniline was isolated by vacuum distillation.

C. 2-Isopropylmercaptoaniline and, N-methylolpyrrolidone were condensed in toluene with the removal of water as described in Example 1.

D. This methylenepyrrolidonylaniline thus formed was further reacted with chloroacetyl chloride in toluene in the presence of sodium carbonate to form the desired product.

EXAMPLE 5

N-Chloroacetyl-N-(N'-Methylenepyrrolidonyl)-2-Butylmercaptoaniline

2-Butylmercaptoaniline was prepared from -2-nitrothiophenol by a two-step reaction sequence consisting of alkylation followed by reduction corresponding to the procedure described in Example 4. The aniline then was condensed with N-methylolpyrrolidone, followed by reaction with chloroacetyl chloride to yield the desired product.

EXAMPLE 6

N-Chloroacetyl-N-(N'-Methylenepyrrolidonyl)-2-Propen-2-yl-mercaptoaniline

2-Propen-2-yl-mercaptoaniline was prepared by reduction of 2-propen-2-yl-mercaptonitrobenzene, which was obtained by condensing 2-nitrothiophenol and allylbromide, to give the corresponding aniline, as described in Example 4. Then 2-propen-2-yl-mercaptoaniline and N-methylolpyrrolidone were condensed in toluene with the removal of water. The methylenepyrrolidonylaniline thus formed was further reacted with chloroacetyl chloride in toluene in the presence of sodium carbonate, as described in Example 1, to form the desired product.

EXAMPLE 7

N-Chloroacetyl-N-(N'-Methylenepyrrolidonyl)-2-Ethoxyethylmercaptoaniline

2-Ethoxyethylmercaptoaniline was prepared by reduction of 2-ethoxyethylmercaptonitrobenzene, which was obtained by condensation of 2-nitrothiophenol and 2-bromoethyl ethyl ether, to give the corresponding aniline. The 2-Ethoxyethylmercaptoaniline and N-methylolpyrrolidone were then condensed in toluene with the removal of water. The methylenepyrrolidonylaniline thus formed was further reacted with chloroacetyl chloride in toluene in the presence of sodium carbonate, to provide the desired product.

EXAMPLE 8

N-Chloroacetyl-N-(N'-Methylenepyrrolidonyl)-2-Cyclopentylmercaptoaniline

2-Cyclopentylmercaptoaniline was prepared by reduction of 2-cyclopentylmercaptonitrobenzene, which was obtained from 2-nitrothiophenol and bromocyclopentane followed by reduction to the corresponding aniline as described in Example 4. The 2-cyclopentylmercaptoaniline was subsequently condensed in toluene with the removal of water. The methylenepyrrolidonylaniline thus formed is further reacted with chloroacetyl chloride in toluene in the presence of sodium carbonate, as described in Example 1, to form the desired product.

EXAMPLE 9

Herbicidal Tests

Primary tests were made on two flats seeded with six species of representative monocotyledonous and dicotyledonous plants (Japanese millet, foxtail millet and crabgrass). The test chemical was applied to one such flat immediately after it was seeded. The other flat contained plants on which the first true leaves had developed. Both of these flats were sprayed, simultaneously, with the test chemical at 2080 ppm, a rate sufficient to give 10 lb/acre (104 mg in 50 ml of water on 144 square inches). Diuron, 3-(3,4-dichlorophenyl)-1,1-dimethylurea, as a standard, was applied pre-emergence at the rate of 2.5 lb/acre. The response was rated 12 to 21 days after treatment on a scale of 0 to 10 where 0 represents no injury and 10 represents complete kill.

TABLE 1

| | Pre-Emergence Herbicidal Ratings | |
|---|---|---|
| | Primary (10 lbs/acre) | |
| Test Plant | Example 1 | Standard (Diuron) |
| Foxtail Millet | 8 | 10 |
| Japanese Millet | 10 | 10 |
| Crabgrass | 10 | 10 |

The tests demonstrate the effectiveness of the compounds of the invention against wild grasses.

While the invention has been described with particular reference to certain embodiments thereof, it will be understood that certain modifications and changes may be made which are within the skill of the art. Therefore it is intended to be bound only by the appended claims.

What we claim is:

1. Herbicidal compounds having the formula:

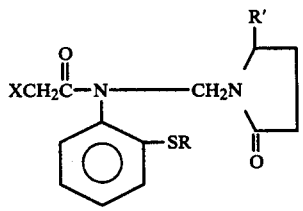

where
R is alkyl having 1-6 carbon atoms, alkenyl having 2-6 carbon atoms, cycloalkyl having 4-6 carbon atoms, unsubstituted or substituted with alkyl of 1-4 carbon atoms, or alkyleneoxyalkyl of 2-8 carbon atoms,
R' is hydrogen or alkyl of 1-3 carbon atoms, and
X is chloro or bromo.

2. Compounds according to claim 1 wherein R is alkyl having 1-6 carbon atoms.

3. Compounds according to claim 1 wherein R is alkenyl having 2-6 carbon atoms.

4. Compounds according to claim 1 wherein R is cycloalkyl having 4-6 carbon atoms, unsubstituted or substituted with alkyl of 1-4 carbon atoms.

5. Compounds according to claim 1 wherein R is alkyleneoxyalkyl of 2-8 carbon atoms.

6. Compounds according to claim 1 wherein R' is hydrogen.

7. Compounds according to claim 1 wherein R' is alkyl of 1-3 carbon atoms.

8. Compounds according to claim 1 wherein X is chloro or bromo.

9. A compound according to claim 1 which is N-chloroacetyl-N-(N'-methylenepyrrolidonyl)2-2-methylmercaptoaniline.

10. A compound according to claim 1 which is N-chloroacetyl-N-(N'-methylenepyrrolidonyl)-2-ethylmercaptoaniline.

11. A compound according to claim 1 which is N-chloroacetyl-N-(5-methyl-N'-methylenepyrrolidonyl)-2-methylmercaptoaniline.

12. A compound according to claim 1 which is N-chloroacetyl-N-(N'-methylenepyrrolidonyl)-2-isopropylmercaptoaniline.

13. A compound according to claim 1 which is N-chloroacetyl-N-(N'-methylenepyrrolidonyl-2-butylmercaptoaniline.

14. A compound according to claim 1 which is N-chloroacetyl-N-(N'-methylenepyrrolidonyl)-2-propen-2-yl-mercaptoaniline.

15. A compound according to claim 1 which is N-chloroacetyl-N-(N'-methylenepyrrolidonyl)-2-ethoxyethylmercaptoaniline.

16. A compound according to claim 1 which is N-chloroacetyl-N-(N'-methylenepyrrolidonyl)-2-cyclopentylmercaptoaniline.

* * * * *